United States Patent
Divi et al.

(10) Patent No.: US 11,884,623 B2
(45) Date of Patent: Jan. 30, 2024

(54) PROCESS FOR THE PREPARATION OF (R)-4-PROPYL PYRROLIDINE-2-ONE, A KEY INTERMEDIATE FOR SYNTHESIS OF BRIVARACETAM

(71) Applicant: DIVI'S LABORATORIES LTD., Telangana (IN)

(72) Inventors: Murali Krishna Prasad Divi, Telangana (IN); Nageswara Rao Bolneni, Telangana (IN); Leela Maheswara Rao Bandarupalli, Telangana (IN)

(73) Assignee: DIVI'S LABORATORIES LTD., Hyderabad (IN)

( * ) Notice: Subject to any disclaimer, the term of this patent is extended or adjusted under 35 U.S.C. 154(b) by 0 days.

(21) Appl. No.: 17/857,325

(22) Filed: Jul. 5, 2022

(65) Prior Publication Data
US 2023/0373914 A1    Nov. 23, 2023

(30) Foreign Application Priority Data
May 23, 2022  (IN) .............................. 202241029449

(51) Int. Cl.
C07D 207/27    (2006.01)
(52) U.S. Cl.
CPC ................................. C07D 207/27 (2013.01)
(58) Field of Classification Search
CPC .................................................... C07D 207/27
See application file for complete search history.

(56) References Cited

U.S. PATENT DOCUMENTS

| | | |
|---|---|---|
| 8,338,621 B2 | 12/2012 | Surtees et al. |
| 8,957,226 B2 | 2/2015 | Ates et al. |
| 10,781,170 B1 | 9/2020 | Divi et al. |
| 2010/0087525 A1 | 4/2010 | Hedvati et al. |

FOREIGN PATENT DOCUMENTS

| | | |
|---|---|---|
| CN | 109266630 B | 2/2021 |
| CN | 113045468 A | 6/2021 |
| EP | 2518050 A1 | 10/2012 |
| WO | 0162726 A2 | 8/2001 |
| WO | 2016075082 A1 | 5/2016 |
| WO | 2020051796 A1 | 3/2020 |
| WO | 2020148731 A1 | 7/2020 |

OTHER PUBLICATIONS

Francis et al. (1984). Preparations of chiral delta-lactones via enantiotopically specific pig liver esterase-catalysed hydrolyses of 3-substituted glutaric acid diesters. J. Chem. Soc., Chem. Commun., No. 9., pp. 579-580.
European Search Report from corresponding EP 22 18 3808 dated Jan. 4, 2023.
Reznikov et al. (2018). Nitroalkenes in the Ni(II) catalyzed asymmetric michael addition. Convenient route to the key intermediate of brivaracetam. Helvetica Chimica Acta, 101.
Li et al. "A novel lipase from Aspergillus oryzae WZ007 catalyzed synthesis of brivaracetam intermediate and its enzymatic characterization" Chirality, vol. 33, Issue 2, 2021, pp. 62-71. DOI: 10.1002/chir.23286.
English abstract for CN 109266630 A (2019).
English abstract for CN 113045468 A (2021).
Examination Report from counterpart IN Patent Application No. 202241029449 dated Mar. 17, 2023.
Zhou et al. "Pig liver esterases PLE1 and PLE6: heterologous expression, hydrolysis of common antibiotics and pharmacological consequences" Scientific Reports (Oct. 29, 2019) (doi: 10.1038/s41598-019-51580-4).

*Primary Examiner* — Kamal A Saeed
(74) *Attorney, Agent, or Firm* — CAESAR RIVISE, PC

(57) ABSTRACT

A process for the preparation of (R)-4-propyl-pyrrolidine-2-one, is provided which includes enzymatic conversion of dimethyl 3-propyl pentanedioate selectively into (S)-3-(2-methoxy-2-oxoethyl) hexanoic acid using Novozyme's Promea® enzyme, amidation of (S)-3-(2-methoxy-2-oxoethyl) hexanoic acid, followed by ester hydrolysis to obtain (S)-3-(2-amino-2-oxoethyl) hexanoic acid having high chiral purity >99% and converting the amide to amine by Hofmann rearrangement and cyclization resulting in (R)-4-propyl-pyrrolidine-2-one. It is further converted to Brivaracetam by N-alkylation with 2-bromobutyric acid, esterification followed by enzymatic resolution.

1 Claim, No Drawings

PROCESS FOR THE PREPARATION OF (R)-4-PROPYL PYRROLIDINE-2-ONE, A KEY INTERMEDIATE FOR SYNTHESIS OF BRIVARACETAM

CROSS-REFERENCE TO RELATED APPLICATIONS

This application claims priority under 35 U.S.C. § 119(a) to Indian Patent Application No. 202241029449, filed May 23, 2022, the contents of which are incorporated herein by reference in their entireties.

FIELD OF THE INVENTION

The present invention relates to an improved process for the preparation of (R)-4-propyl-pyrrolidine-2-one, a key intermediate for the synthesis of Brivaracetam, a drug useful in treating epilepsy and related central nervous system disorders.

BACKGROUND OF THE INVENTION

Brivaracetam is chemically (2S)-2-[(4R)-2-oxo-4-propyl-pyrrolidin-1-yl] butanamide, having the structure:

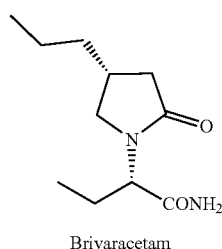

Brivaracetam

Brivaracetam and its process for preparation were first disclosed in WO 01/62726. The compound, 5-hydroxy-4-propyl-furan-2-one is condensed with S-2-aminobutyramide through reductive amination followed by further reduction to give racemic Brivaracetam. Further, the racemic Brivaracetam is resolved using chiral chromatography.

The U.S. Pat. No. 8,957,226 B2 describes the synthesis of Brivaracetam, where hex-2-enoic acid ethyl ester is reacted with nitromethane followed by reduction resulting in racemic lactam, which is then resolved using chiral chromatography to obtain (R)-4-propyl-pyrrolidin-2-one followed by further reaction with racemic methyl ester of 2-bromobutyric acid and amidation with ammonia resulting in racemic Brivaracetam. A second chiral chromatography for the resolution of the racemic mixture results in the required drug substance Brivaracetam.

The U.S. Pat. No. 8,338,621 B2 describes condensation of (R)-4-propyl-pyrrolidin-2-one, with (R)-2-bromobutyric acid to obtain (S)-2-[(S)4-propyl-2-oxopyrrolidin-1-yl] butyric acid, which can be converted into Brivaracetam. However, the patent does not provide the process for the preparation of Brivaracetam intermediates. Thus, (R)-4-propyl-pyrrolidin-2-one is a key intermediate for the preparation of Brivaracetam.

A process for the preparation of (R)-4-propyl-pyrrolidin-2-one is described in WO 2016075082 A1 (Scheme 1). It involves selective amination of racemic aldehyde using the enzyme ω-transaminase to obtain (R)-amine followed by cyclization. The enzyme has been obtained from several microorganisms of which one from *Hyphomonas neptunium* exhibited highest selectivity with 92% ee and 65% yield. The enzyme is not commercially available and needs expensive laboratory preparation. Moreover, they need amino donor compounds (mole equivalents or more) and cofactor pyridoxal or pyridoxamine phosphates.

Scheme 1

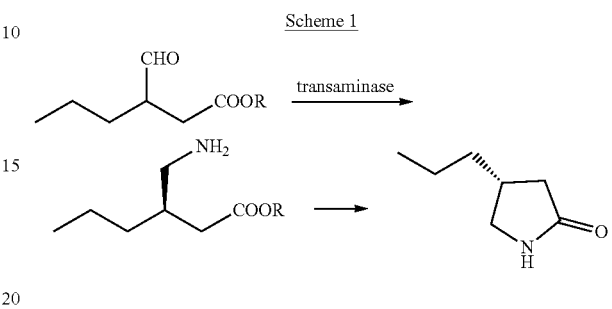

Reznikov et al (*Helvetica Chimica Acta*, 2018, 101, doi.org/10.1002/hlca.201800170) reported a chiral synthesis of (R)-4-propyl-pyrrolidin-2-one by asymmetric Michael addition using Nickel catalysts. Reaction of 1-nitropent-1-ene with diethylmalonate in the presence of Ni(II) complex with chiral ligand (IR,2R)-1,2-diphenylethane-1,2-diamine catalyst results in chiral nitro malonate derivative which on hydrogenation results predominantly (3R,4R) isomer ester. Base catalyzed hydrolysis of the ester followed by decarboxylation by refluxing in toluene results in (R)-4-propyl-pyrrolidin-2-one (Scheme 2).

Scheme 2

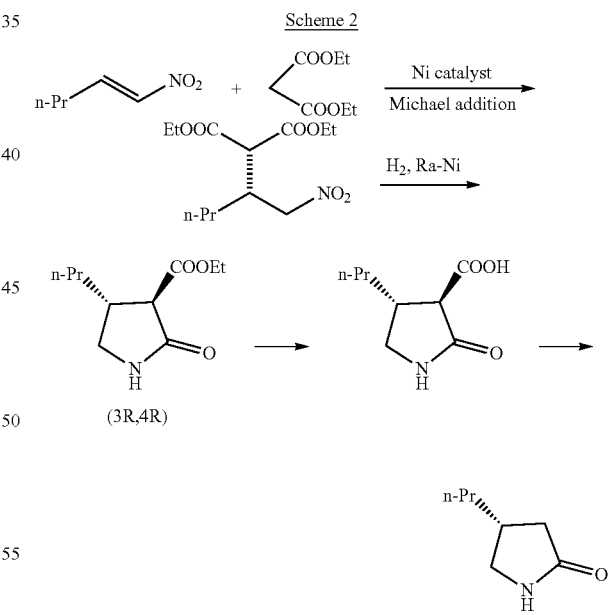

Yet another process for the preparation of (R)-4-propyl-pyrrolidin-2-one is described in WO 2020051796A1 (Scheme 3) which describes the asymmetric desymmetrization method for the ring opening of 3-n-propylglutaric anhydride with an alcohol in the presence of a quinine derivative chiral catalyst Q-BTBSA, followed by amidation, Hofmann rearrangement and cyclization to give the required (R)-4-propyl-pyrrolidin-2-one.

Scheme 3

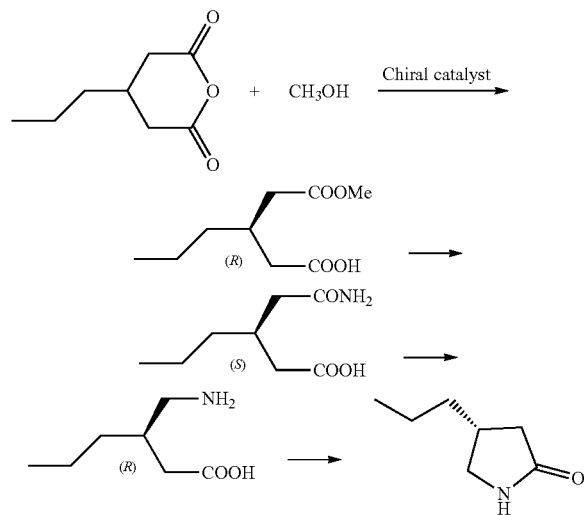

Another process described in WO 2020/148731 A1 (Scheme 4) starts with 3-propyl glutaric anhydride, which is reacted with (R)-(+)-phenylethylamine to give chiral glutarimide derivative and further treated with aqueous sodium hydroxide to obtain (3R)-3-[2-oxo-2-[[(1R)-1-phenyethyl]amino] ethylhexanoic acid. Conversion of the free carboxylic acid to amine via Curtius rearrangement using sodium azide, subsequent hydrolysis and cyclization in presence of para toluene sulfonic acid results in the required (R)-4-propyl-pyrrolidin-2-one. Handling sodium azide, a highly toxic chemical, on industrial scale is not advisable. The starting material, 3-propyl glutaric anhydride had been prepared commonly by heating a mixture of 3-propyl glutaric acid and acetic anhydride. Acetic anhydride is now a controlled chemical listed in the UN convention against illicit traffic in narcotic drugs and psychotropic substances.

Scheme 4

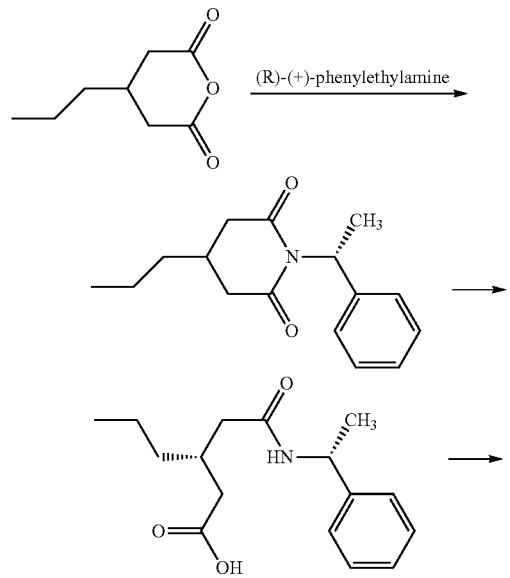

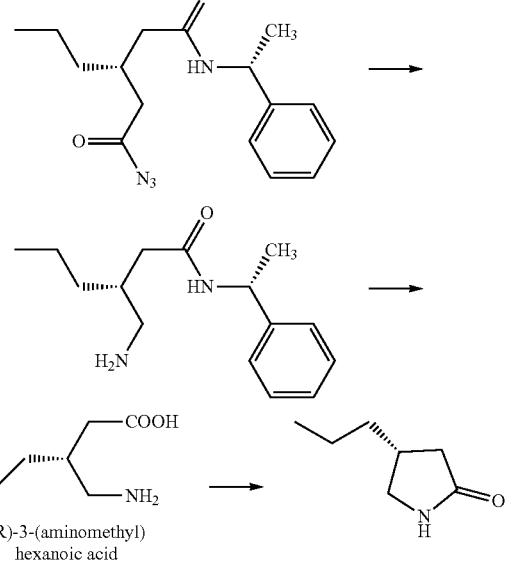

The process for the preparation of (R)-4-propyl-pyrrolidin-2-one is described in US B1 (Scheme 5) starting from 4-propyl piperidine-2, 6-dione to obtain racemic 3-(2-amino-2-oxoethyl) hexanoic acid, which on classical resolution using (S)-(−)-1-phenylethylamine gives required (S)-enantiomer. Further chlorination of (S)-3-(2-amino-2-oxoethyl) hexanoic acid to obtain the (S)-3-(2-(chloroamino)-2-oxoethyl) hexanoic acid, Hofmann rearrangement, followed by cyclization in one pot reaction, gives the required (R)-4-propyl-pyrrolidin-2-one.

Scheme 5

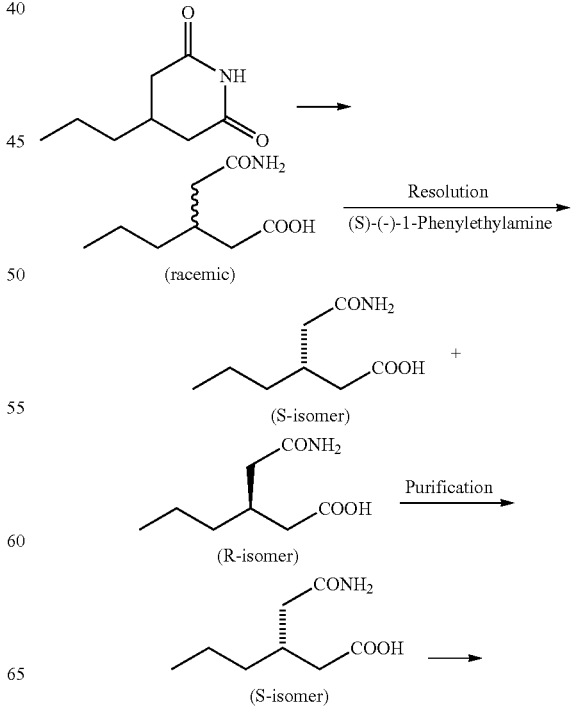

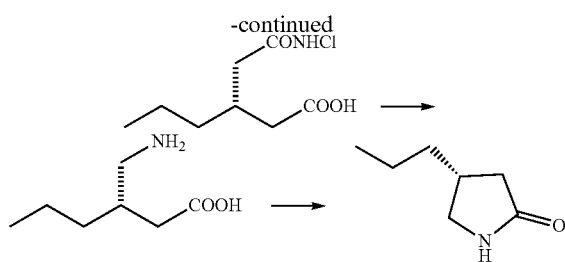

All prior art processes for the preparation of the key intermediate, (R)-4-propyl pyrrolidin-2-one are multi stages with a major stage of resolution with yields of less than 40%. Recovery of unwanted isomer and racemization for recycling are tedious and expensive.

Thus, there is a need for a better process which is environmentally safe and can be applied on industrial scale in a cost-effective manner for the preparation of (R)-4-propyl-pyrrolidin 2-one.

SUMMARY OF THE INVENTION

The present invention describes a novel process for the preparation of the key intermediate (R)-4-propyl-pyrrolidin-2-one (I), which can be converted to Brivaracetam, involving an enzymatic asymmetric desymmetrization technique using commercially available Novozyme's Promea®, a lipase liquid enzyme (EC 3.1.1.3; CAS No. 9001-62-1), without using any organic solvent as shown in the scheme 6 below:

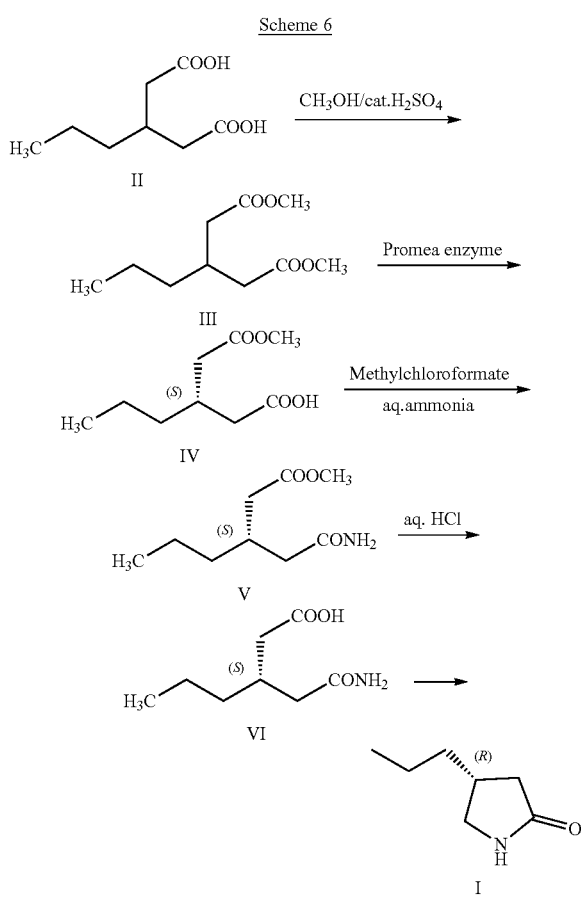

The process comprises esterification of 3-propylpentanedioic acid (II) to obtain dimethyl 3-propylpentanedioate (III), which is selectively hydrolysed under asymmetric desymmetrization method by using biocatalyst Novozyme's Promea® (EC 3.1.1.3) in a suitable buffer, giving predominantly (S)-3-(2-methoxy-2-oxoethyl) hexanoic acid (IV). Converting the free carboxylic acid of (IV) into amide (V) using methyl chloroformate and ammonia in the presence of base. The ester hydrolysis of (V) using aqueous HCl gives pure (S)-3-(2-amino-2-oxoethyl) hexanoic acid (VI) with >99% ee, which on Hoffmann rearrangement followed by cyclization results in (R)-4-propyl-pyrrolidin-2-one (I). The intermediate (I) is converted to Brivaracetam through prior art methods.

Thus, the present invention describes a new process for the preparation of (I) by enzymatic method using less expensive and commercially available enzyme.

It avoids the use of expensive quinine derivative chiral catalyst Q-BTBSA (scheme 3), hazardous sodium azide and chiral amine auxiliary phenyl ethylamine (Scheme-4) as described in prior art methods.

An earlier prior art process by classical resolution (non-enzymatic, scheme-5) involves multiple steps, racemic monoacid amide salt formation with S-phenyl ethyl amine in chloroform/ethanol mixture, isolation, purification, later salt breaking to get single isomer product, recovery of chiral base S-phenyl ethyl amine, recovery of unwanted isomer and racemization. Use of enzymatic process has eliminated the need for these additional steps.

DETAILED DESCRIPTION OF THE INVENTION

The present invention provides a novel process for the preparation of (R)-4-propyl-pyrrolidin-2-one comprising the steps of:
(a) esterification of 3-propylpentanedioic acid of formula (II) to produce dimethyl 3-propylpentanedioate of formula (III),
(b) using aymmetric desymmetrization technique and stereoselective hydrolysis of formula (III) with Novozyme's Promea® to obtain (S)-3-(2-methoxy-2-oxoethyl) hexanoic acid of formula (IV),
(c) subjecting the compound (IV) to activation of carboxylic acid and followed by amidation, in one pot, to obtain methyl (S)-3-(2-amino-2-oxoethyl) hexanoate of formula (V), and
(d) reacting the compound (V) with an acid to produce (S)-3-(2-amino-2-oxoethyl) hexanoic acid of formula (VI),
(e) Hofmann rearrangement of compound (VI) followed by cyclization to obtain (R)-4-propyl-pyrrolidin-2-one (I) and
(f) converting the product of formula (I) into Brivaracetam.

The required starting material, 3-propylpentanedioic acid of formula (II) prepared by the method was reported in U.S. Pat. No. 10,781,170 B1. Esterification of diacid (II), in methanol using suitable acid, preferably sulphuric acid, gives (Ill) in good yield and purity.

The stereoselective enzymatic hydrolysis of dimethyl ester (Ill) to (S)-3-(2-methoxy-2-oxoethyl) hexanoic acid of formula (IV) was initially studied with various commercially available protease enzymes from *Bacillus licheniformis*, EC 3.4.21.62, Sigma (alcalase) and subtilisin Carlsberg (Bacterial alkaline protease, EC. 3.4.21.62). However, both failed to hydrolyse the ester (III). Next, different lipases available commercially, Lipase from *Rhizopus oryzae* 62305, Lipase from Porcine pancreas L3126, Lipase from *Rhizopus niveus* 62310, Lipase from *Candida rugosa* 62316, Lipase from *Pseudomonas cepacia* 62309, Lipase from *Mucor miehei* 62298, Lipase from *Aspergillus niger* 62301 and Lipase from *Pseudomonas fluorescens* 89601 (EC. 3.1.1.3, from Sigma) were studied. All failed to hydrolyse the ester (III). However, during the screening, surprisingly, Novozyme's Promea® lipase liquid enzyme (EC 3.1.1.3) resulted in selectively hydrolysing (S)-3-(2-methoxy-2-oxoethyl) hexanoic acid (IV), in a buffer, in excellent yield (>95%) and chiral purity (83-88% ee and >99% chemical purity).

Using Novozyme's Promea® enzyme stereoselective enzymatic hydrolysis was studied with different substrates like diester derivatives of compound III (diethyl, di-2-chloroethyl and n-propyl) with results of lower chiral purity of the product and with other diester derivatives of compound III (di-isopropyl and di-n-butyl), no conversion was observed.

The enzymatic reaction was carried out by stirring dimethyl 3-propylpentanedioate (III) in phosphate buffer (0.2M, 7.2 pH) at 25 (±5) ° C., to which Promea 5000 LU/g was added and stirred. Throughout the reaction pH was maintained by adding 10% ammonium hydroxide solution using pH stat. Completion of the reaction was monitored by TLC, also indicated when the consumption of ammonium hydroxide stopped. The reaction mixture was acidified to pH 2.0 using conc. HCl and extracted with an organic solvent selected from the group consisting of dichloromethane, ethyl acetate and isopropyl acetate. The organic layer was washed with water and dried over sodium sulphate. The organic layer was concentrated under reduced pressure to yield (S)-3-(2-methoxy-2-oxoethyl) hexanoic acid (IV).

The enzyme load range from 1 to 20% w/w was studied. With 20% w/w the reaction completes in about 3 to 5 hours. When the reaction was carried out with 2.5% w/w, it requires about 20 to 24 hours to complete the reaction. In both cases, yield (>95%) and chiral purity (85%) were similar. When enzyme load was reduced to 1%, conversion was very slow requiring about 3 days. The optimum enzyme load was found to be 2.5% w/w and reaction time 20 to 24 hours.

The optimum reaction temperature is about 15° C. and 30° C. At lower temp (0-5° C.) reaction is very slow and incomplete conversion even after 48 hours. The pH of the reaction medium is between 6.0 and 9.0, preferably 7.2.

The reaction of compound (IV) with methyl chloroformate is best carried out in the presence of an organic base such as n-methyl morpholine or triethyl amine in a suitable solvent such as dichloromethane at temperature between −20° C. to −10° C. and followed by reaction with aqueous ammonia to obtain methyl (S)-3-(2-amino-2-oxoethyl) hexanoate (V) with yield of 90% and chiral purity of 83-85% ee and chemical purity of 97-99% by GC.

The ester hydrolysis of compound (V) with a suitable acid, such as aqueous hydrochloric acid, preferably 1.0M to 4.0M solution, more preferably 1.5M to 2.0M solution, at temperature between 20° C. and 40° C., preferably 25° C. for about 20 to 24 hours to obtain (S)-3-(2-amino-2-oxoethyl) hexanoic acid (VI) with yield of 45-50% and chiral purity (>99% ee). When the reaction was carried out with 48% aq. HBr, a major amount of diacid (II) is formed. When reaction was tried with HCl or perchloric acid in 1,4-dioxane very low conversion was observed. No conversion was found with other acids tried: 5% aq·$H_2SO_4$, 85% aq. $H_3PO_4$, formic acid, trifluoroacetic acid and acetic acid. Reaction in presence of bases sodium hydroxide and lithium hydroxide resulted in racemic product and in aqueous ammonia major amount of glutarimide product was formed. Enzymatic methods were also tried with different enzymes like Amano Lipase from *Pseudomonas*, Novozyme 435 (N435) (an immobilized lipase), Alcalase® a protease from *Bacillus licheniformis* and Lipase from *Candida rugosa*. All resulted in no conversion.

The compound (VI) obtained by the enzymatic process of the present invention was in high yields and purity compared to the classical resolution methods.

After isolating the pure product (VI), the filtrate containing mixture of isomers, unreacted starting material (V) and other products was treated with aqueous HCl, heated at 100 to 110° C. for about 15 hours resulting in recovery of (II). The chirality of both (VI) and (V) in the filtrate gets eliminated when converted to (II), which is a symmetrical molecule.

The chirally pure (S)-3-(2-amino-2-oxoethyl) hexanoic acid (VI), carried out Hofmann rearrangement using chlorinating agent such as trichloroisocyanuric acid and sodium hydroxide in water, followed by cyclization to produce (R)-4-propy-pyrrolidin-2-one (I), with high chiral purity (>99% ee). The chirally pure (R)-4-propyl-pyrrolidin-2-one (I) reacted with racemic 2-bromobutyric acid, followed by esterification using methanol and sulphuric acid to obtain (2RS)-2-[(4R)-2-oxo-4-propylpyrrolidin-1-yl] butyric acid methyl ester, which by reacting with protease from *Bacillus licheniformis* could be converted to (2S)-2-[(4R)-2-oxo-4-propylpyrrolidin-1-yl] butyric acid, and then to Brivaracetam through prior art method.

The embodiments of the present invention are further described in the following examples, which are not intended in any way to limit the scope of the invention.

EXAMPLES

Analytical Methods:
Chemical purity was determined using HPLC under the following conditions: Column: Inertsil ODS 3V, 250×4.6 mm, 5 μm. Mobile phase: acetonitrile: buffer (0.1% orthophosphoric acid) (90:10 v/v); flow rate: 1.0 mL/min; column temperature: 30° C. and detection: 210 nm.

Chemical purity was determined using GC under the following conditions: Column: DB-1, meters, 0.53 mm, 1.5 μm. diluent: dichloromethane, Carrier gas: He and Column oven temperature: 100° C. to 250° C.

Enantiomeric purity was determined using HPLC under the following conditions:
Column: Chiral Pak IC 250×4.6 mm, 5 μm.
Method-A for Compound (IV):
Mobile phase:n-hexane:ethanol:trifluoro acetic acid (98:2:0.1 mL), flow rate: 0.5 mL/min. Column temperature: 25° C., detection: 212 nm.
Method-B for Compound (V) and (VI):
Mobile phase:n-hexane:ethanol:trifluoro acetic acid (80:20:0.1 mL), flow rate: 1.0 mL/min. Column temperature: 25° C., detection: 220 nm.
Method-C for Compound (I):
Mobile phase:n-hexane:ethanol:trifluoro acetic acid (70:30:0.1 mL), flow rate: 1.0 mL/min. Column temperature: 27° C., detection: 210 nm.

Example-1: Preparation of dimethyl 3-propylpentanedioate (III)

Sulphuric acid (14.2 g, 0.14 mol) was added to a solution of 3-propylpentanedioic acid (100 g, 0.57 mol) in 300 mL of methanol at 15° C. to 20° C. The reaction mixture was warmed and stirred at room temperature for about 20 hours to complete the reaction. The solvent was evaporated under reduced pressure, the obtained residue was diluted with 50 mL of water and extracted with dichloromethane (100 mL×3). The dichloromethane solution was washed with 10% sodium bicarbonate solution, followed by water (100 mL). The organic phase was dried over sodium sulphate and evaporated under reduced pressure to obtain crude product, which was purified by high vacuum distillation. Pure product was collected at vapour temperature 80° C. to 90° C., 0.5 mmHg to obtain 94.8 g of colourless dimethyl 3-propylpentanedioate (III). (82% yield and 99.05% purity by GC).

Example-2: Preparation of (S)-3-(2-methoxy-2-oxoethyl) hexanoic acid (IV)

To a solution of potassium phosphate buffer (50 mL, 0.2M, pH 7.2) was added 10 g (0.05 mol) of dimethyl 3-propylpentanedioate (III) and stirred at 25 (±5) ° C. To the reaction mixture was added 0.25 g (2.5% w/w) Promea [Novozyme's Promea® is a Lipase liquid enzyme (EC 3.1.1.3; CAS No. 9001-62-1), 5000 LU/g] maintaining the pH at 7.2 using 10% ammonium hydroxide solution with the help of pH stat for 24 hours. Completion of the reaction was monitored by TLC. The reaction mixture was adjusted to pH 2.0 using con. HCl and extracted with dichloromethane (50 mL×2). The organic layer was washed with water and dried over sodium sulphate. The organic layer was concentrated under reduced pressure resulting in 9.1 g of (S)-3-(2-methoxy-2-oxoethyl) hexanoic acid (IV). 97.8% yield, ee by HPLC and 99.56% purity by GC.

Example-3: Preparation of (S)-3-(2-methoxy-2-oxoethyl) hexanoic acid (IV)

The above example-2 was repeated with 20% w/w enzyme loading, instead of 2.5% w/w. Reaction was completed in about 4 hours. 96.7% yield, 85.8% ee and 99.38% purity by GC.

Example-4: Preparation of (S)-3-(2-methoxy-2-oxoethyl) hexanoic acid (IV)

The above example-2 was repeated with 10% w/w enzyme loading, instead of 2.5% w/w. Reaction was completed in about 6 hours. 98.9% yield, 84.35% ee and 99.68% purity by GC.

Example-5: Preparation of (S)-3-(2-methoxy-2-oxoethyl) hexanoic acid (IV)

The above example-2 was repeated with 5% w/w enzyme loading, instead of 2.5% w/w. Reaction was completed in about 18 hours. 96.7% yield, 83.82% ee and 99.47% purity by GC.

Example-6: Preparation of (S)-3-(2-methoxy-2-oxoethyl) hexanoic acid (IV)

The above example-2 was repeated with 1% w/w enzyme loading, instead of 2.5% w/w. Reaction was completed in about 68 hours. 92.5% yield, 82.97% ee and 99.41% purity by GC.

Example-7: Preparation of methyl (S)-3-(2-amino-2-oxoethyl) hexanoate (V)

To a cooled solution of 50 g (0.266 mol) of (S)-3-(2-methoxy-2-oxoethyl) hexanoic acid (IV) and N-methylmorpholine (40.3 g, 0.398 mol) in 500 mL dichloromethane was added dropwise methyl chloroformate (27.6 g, 0.292 mol) at −15° C. After stirring for 60 minutes, aqueous ammonia (220 mL) was added dropwise for 20 minutes and the mixture was further stirred for 60 minutes to complete the reaction. The reaction mixture was allowed to cool to room temperature and the layers separated. The aqueous layer was re-extracted with dichloromethane. Both organic layers combined, dried over anhydrous sodium sulphate and concentrated to obtain crude product. It was slurried in hexanes (100 mL) at 25-30° C. for 10 minutes, decanted and high vacuum applied to obtain 44.3 g of methyl (S)-3-(2-amino-2-oxoethyl) hexanoate (V) as semi solid. 89% yield, 84.44% ee by HPLC and 97.66% purity by GC.

Example-8: Preparation of methyl (S)-3-(2-amino-2-oxoethyl) hexanoate (V)

The above example-7 was repeated with triethylamine, instead of N-methylmorpholine. 93.5% yield and 83.25% ee.

Example-9: Preparation of (S)-3-(2-amino-2-oxoethyl) hexanoic acid (VI)

A mixture of 10 g methyl (S)-3-(2-amino-2-oxoethyl) hexanoate (V) and 100 mL of 1.8M aqueous HCl (15 mL of con. HCl and 85 mL of water) was stirred at 25 (±5) ° C. for 20 hours. The reaction mixture was cooled to 5° C., pH adjusted 1.0 using C.S. Lye solution and stirred for 30 minutes. The obtained solid was filtered and dried. It was slurried in ethyl acetate (20 mL) at 25 (±5) ° C. for 60 minutes and filtered to obtain 4.5 g of (VI) solid, 48.6% yield, 99.95% ee by HPLC and 99.28% purity by HPLC.

Recovery of (II) from Filtrate:

Both the above filtrates were mixed and concentrated under reduced pressure at 50° C. The obtained crude product was dissolved in water (30 mL) and con. HCl (30 mL) mixture, heated to 100° C. and stirred for 15 hours. The reaction mixture was cooled to 25 (±3) ° C. and extracted with dichloromethane (25 mL×2). The organic layer dried over anhydrous sodium sulphate and concentrated to obtain 4.2 g of 3-propylpentanedioic acid (II). 99.19% purity by GC.

Example-10: Preparation of (S)-3-(2-amino-2-oxoethyl) hexanoic acid (VI)

The above example-9 was repeated with 3.6M aqueous HCl (50 mL), instead of 1.8M aqueous HCl (100 mL). 35% yield, 99.55% ee by HPLC and 97.97% purity by HPLC.

Example-11: Preparation of (R)-4-propy-pyrrolidin-2-one (I)

To a solution of sodium hydroxide (4.62 g, 0.116 mol) in water (80 mL) stirred at 0-5° C., (S)-3-(2-amino-2-oxoethyl) hexanoic acid (VI) (4.0 gm, 0.023 mol) was added. To the reaction mixture trichloroisocyanuric acid 2.15 g (0.009 mol) was added portion wise during 30 minutes at 0-5° C., allowed to rise to room temperature and continued to for 12 to 15 hours. The reaction mixture was heated to 100° C. and 120° C. and stirred for 45 to 48 hours. It was then cooled to 25° C. and 30 mL of dichloromethane (DCM) added and stirred for 10 minutes. The DCM layer was separated and aqueous layer re-extracted with DCM. Both organic layers were mixed, dried over anhydrous sodium sulphate and concentrated to remove the solvent completely under reduced pressure to obtain (R)-4-propyl-pyrrolidin-2-one (I) of 2.18 gm (74.14% yield) as a liquid, 99.96% ee and 99.39% purity by GC.

Example-12: Preparation of Brivaracetam from (I)

To a mixture of sodium hydride (60% oily dispersion, 7.54 g, 0.3144 mol) in 50 mL tetrahydrofuran was added a solution of (R)-4-propyl-pyrrolidin-2-one (I) (10.0 g, 0.0786 mol) in 30 mL tetrahydrofuran at 0-5° C. To the mixture was added a solution of 2-bromo butanoic acid (15.75 g, 0.094 mol) in 20 mL tetrahydrofuran. The reaction mixture was warmed and stirred at room temperature for 10-12 hours. The mixture was poured into crushed ice to decompose excess sodium hydride. Tetrahydrofuran was distilled under reduced pressure and the aqueous residue was adjusted to pH 2.0 at 0-5° C. using hydrochloric acid. The residue was extracted with isopropyl acetate (25 mL×3). The organic layer was concentrated to obtain (2RS)-2-[(4R)-4-propyl-2-oxopyrrolidin-1-yl] butyric as a colourless solid (15.8 g, 94.2%).

The above acid (10 g, 0.046 mol), was dissolved in 100 mL methanol. To this was added concentrated sulphuric acid (0.45 g, 0.0045 mol) and maintained at room temperature for 12 hours. The solution was concentrated under reduced pressure. To the residue was added 50 mL cold water and extracted with dichloromethane (25 mL×3). The dichloromethane solution was washed with saturated sodium bicarbonate solution followed by water. After drying over anhydrous sodium sulphate, the solution was concentrated under reduced pressure to obtain 9.2 g of (2RS)-2-[(4R)-4-propyl-2-oxopyrrolidin-1-yl] butyric acid methyl ester as a yellowish oil (Yield=86.38%, G.C: 99.4%).

To a solution of potassium phosphate buffer (120 mL, 0.2 M, pH 7.2) was added 12.0 g (0.0528 mol) of (2RS)-2-[(4R)-4-propyl-2-oxopyrrolidin-1-yl] butyric acid methyl ester and stirred at 27(±2) ° C. To the reaction mixture was added 2.4 G alcalase (protease from Bacillus licheniformis, EC. 3.4.21.62, Sigma, Product Number: P4860, 2.58 U/g) and stirred for about 10 hours maintaining the pH at 7.2 using 10% ammonium hydroxide solution with the help of a pH Stat. The reaction mixture was extracted with n-hexanes to recover the unreacted starting material (unwanted isomer). The pH of the aqueous layer was adjusted to 2.0 using 5N HCl and extracted with isopropyl acetate. The organic layer was washed with water and dried over anhydrous sodium sulphate. Concentration of the organic layer under reduced pressure resulted in 4.83 g of (2S)-2-[(4R)-2-oxo-4-propylpyrrolidin-1-yl] butanoic acid. Yield=80.5%, purity 99.3% (HPLC), Chiral purity: 99.4% (HPLC).

To a cooled solution of 10. g (0.046 mol) of (2S)-2-((R)-2-oxo-4-propylpyrrolidin-1-yl) butanoic acid and triethyl amine (7.1 g, 0.07 mol) in 100 mL dichloromethane was added dropwise ethyl chloroformate 5.54 g (0.05 mol) at −150 C. After stirring for 30 minutes, ammonia gas was passed, and the mixture was stirred for 2 hours at −15° C., and for 1 hour at 25-30° C. Salts were filtered and the filtrate was washed with a solution of potassium carbonate (10% solution, 50 mL×2) to remove unreacted acid. The organic layer was dried over anhydrous sodium sulphate and concentrated to obtain colourless solid. It was slurried in isopropyl acetate (15 mL) at 0-5° C. for 30 minutes and filtered to obtain 8.79 g of Brivaracetam as colourless solid (Yield=88%, H PLC: 99.6, Chiral H PLC: 99.8%).

We claim:

1. A process for the preparation of (2S)-2-[(4R)-2-oxo-4-propyl-pyrrolidin-1-yl] butanamide (brivaracetam) having the structure:

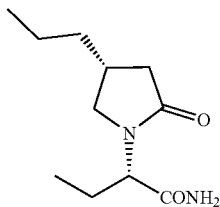

comprising:

(a) stereoselective hydrolysis of dimethyl 3-propylpentanedioate of formula (III)

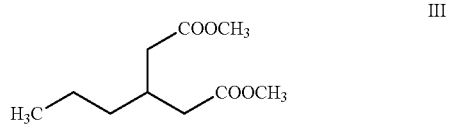

using Novozyme's Promea®, a lipase liquid enzyme having the enzyme commission designation EC 3.1.1.3, in the presence of a buffer solution at a pH from 7.0 to 9.0 and a temperature from 15° C. to 30° C. to obtain (S)-3-(2-methoxy-2-oxoethyl) hexanoic acid of formula IV

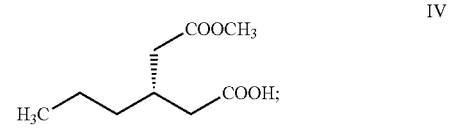

(b) reacting the compound of formula (IV) with ammonia in dichloromethane, in the presence of methyl chloroformate and base N-methylmorpholine or triethylamine at a temperature from −20° C. to 0° C. to obtain methyl (S)-3-(2-amino-2-oxoethyl) hexanoate of formula V

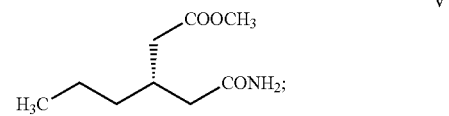

(c) reacting the compound of formula (V) with hydrochloric acid in the range from 1.0M to 4.0M solution at a temperature from 20° C. to 40° C. to obtain (S)-3-(2-amino-2-oxoethyl) hexanoic acid of formula VI

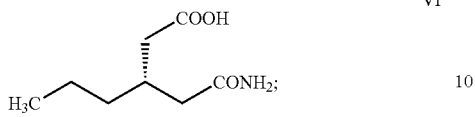

VI (d) converting the compound of formula (VI) by Hofmann rearrangement using tricholoroisocyanuric acid and sodium hydroxide in water at a temperature from 15° C. to 30° C., and later at a temperature from 85° C. and 100° C. to obtain (R)-4-propyl-pyrrolidin-2-one (I)

I and (e) converting the compound of formula (I) into (2S)-2-[(4R)-2-oxo-4-propyl-pyrrolidin-1-yl]butanamide (brivaracetam).

\* \* \* \* \*